United States Patent [19]

Yukawa et al.

[11] 4,427,774

[45] Jan. 24, 1984

[54] PROCESS FOR PRODUCING L-THREONINE

[75] Inventors: Hideaki Yukawa; Terukazu Nara; Yoshihiro Takayama, all of Ibaraki, Japan

[73] Assignee: Mitsubishi Petrochemical Co., Ltd., Tokyo, Japan

[21] Appl. No.: 358,952

[22] Filed: Mar. 17, 1982

[30] Foreign Application Priority Data

Mar. 23, 1981 [JP] Japan .................................. 56-40374

[51] Int. Cl.³ ........................ C12P 13/08; C12N 1/32; C12N 1/20
[52] U.S. Cl. ................................... 435/115; 435/247; 435/253
[58] Field of Search ........................ 435/115, 247, 253

[56] References Cited

U.S. PATENT DOCUMENTS 3,616,217 10/1971 Watanabe et al. .................. 435/115
3,647,628 3/1972 Nakayama ............................ 435/115
3,732,144 5/1973 Nakayama et al. ................. 435/115
3,920,520 11/1975 Tanaka et al. ....................... 435/115
4,276,380 6/1981 Yukama et al. ..................... 435/115

FOREIGN PATENT DOCUMENTS 52-7488 1/1977 Japan .
56-127096 10/1981 Japan .

OTHER PUBLICATIONS

Production of L-Methionine by Fermentation, Chemical Abstracts, vol. 96: 33358h, Feb. 1, 1982, (p. 505).

Primary Examiner—David M. Naff
Attorney, Agent, or Firm—Sughrue, Mion, Zinn, Macpeak & Seas

[57] ABSTRACT

L-threonine is produced by aerobically culturing a bacterium belonging to the genus Acinetobacter, which utilizes ethanol and has an ability to produce and accumulate L-threonine, in a culture medium in which ethanol is the main carbon source to produce and accumulate L-threonine in a culture liquor and recovering L-threonine from the culture liquor. The bacterium is preferably a mutant of *Acinetobacter calcoaceticus* YK-1011 (Ferm-P No. 5910).

7 Claims, No Drawings

PROCESS FOR PRODUCING L-THREONINE

FIELD OF THE INVENTION

The present invention relates to a process for producing L-threonine by fermentation. L-threonine is useful as essential amino acids incorporated into medicines, diets, etc. and its economical production on a commercial scale is needed.

BACKGROUND OF THE INVENTION

Production of amino acids by the fermentation has been practiced using saccharides (carbohydrates) as the main starting materials, but it suffers from various problems such as high cost, unstable supply, transportation and preservation due to the fact that the starting materials are agricultural products. It also suffers from various problems that copious amounts of by-products derived from a large proportion of impurities contained in the starting material are produced, resulting in difficult purification, colored waste water is generated from the fermentation process, etc. Therefore, fundamental improvements have been sought.

As one alternative, a process using hydrocarbons as the starting materials has been studied, but even this process has a drawback that some hydrocarbons are gaseous and some are not soluble in water, which greatly restricts their application on a commercial scale and, as a result, the yield is limited.

SUMMARY OF THE INVENTION

A principal object of the present invention is to provide an economical process for producing L-threonine on a commercial scale.

Another object of the present invention is to provide a process for producing L-threonine from a starting material which is readily available and inexpensive.

Another object of the present invention is to provide a process for producing L-threonine by fermentation of ethanol.

A still further object of the present invention is to provide a bacterium of the genus Acinetobacter which is capable of producing amino acids by fermentation of ethanol.

In view of the foregoing, the present inventors have investigated using ethanol as a starting material for the production of amino acids. Ethanol is expected to be in steady supply and available cheaply and has none of the above disadvantages. As a result, certain bacteria which have an ability to produce and accumulate a remarkable amount of L-threonine when cultured in a medium in which ethanol is the main carbon source have been discovered among the bacteria belonging to the genus Acinetobacter. Thus, the present invention provides a process for producing L-threonine by aerobically culturing bacteria belonging to the genus Acinetobacter, which utilizes ethanol, and which has the ability to produce and accumulate L-threonine in a culture medium in which ethanol is the main carbon source.

DETAILED DESCRIPTION OF THE INVENTION

The bacteria used in the present invention may be any strains belonging to the genus Acinetobacter, provided they utilize ethanol, and have the ability to produce and accumulate L-threonine.

An example of the bacteria which produces and accumulates L-threonine from ethanol is *Acinetobacter calcoaceticus* YK-1014 which has been deposited with the Fermentation Research Institute, the Agency of Industrial Science and Technology, Japan as FERM-P No. 5910 (deposited on Mar. 16, 1981).

This bacterium is derived and isolated from *Acinetobacter calcoaceticus* YK-1011 which has been deposited with the Fermentation Research Institute, the Agency of Industrial Science and Technology, Japan as FERM-P No. 4818 (deposited on Feb. 9, 1979) as the DL-ethionine resistant strain, which has been isolated from *Acinetobacter calcoaceticus* ATCC 19606 as the 5-methyl-DL-tryptophane resistant strain.

The method for deriving the DL-ethionine resistant strain from YK-1011 is explained below.

The growth of the YK-1011 was almost completely inhibited in a plate culture medium prepared by adding 4 mg/ml of DL-ethionine to an artificial culture medium prepared by sterilizing a mixture of 2.0 g Urea, 7.0 g ammonium sulfate, 0.5 g $KH_2PO_4$, 0.5 g $K_2HPO_4$, 0.5 g $MgSO_4.7H_2O$, 2 mg $FeSO_4.7H_2O$, 2 mg $MnSO_4.4-6H_2O$, 2 mg NaCl, 2 mg $CaCl_2.2H_2O$, 2 mg $ZnSO_4.7H_2O$ and 1 liter water at 120° C. for 15 minutes and adding 2% v/v ethanol. The plate was prepared by adding 20 g/l of agar powder to the above artificial culture medium and after sterilization, adding 2% v/v ethanol. The derivation of its mutant was carried out by subjecting it to the N-methyl-N'-nitro-N-nitrosoguanidine treatment (N-methyl-N'-nitro-N-nitrosoguanidine 200 μg/ml, 30° C., 15 minutes, pH 7.0 by trismaleic acid buffer; E. A. Adelberg et al, Biochem, Biophys. Res. Comm. 18, 788 (1965)) in a known manner, culturing it on the plate culture medium containing 4 mg/ml of DL-ethionine as above at 30° C. for 3 to 5 days and isolating the colony produced. Needless to say the derivation of the mutant is not limited to the above nitrosoguanidine treatment and can be effected by ultra-violet irradiation or treatment with various chemicals.

The preferred embodiment for the practice of the present invention is described as follows.

Ethanol is used as the carbon source in the culture medium and the initial concentration is suitably chosen in a range of about 1 to 5% v/v depending on the particular strain used. With its consumption, ethanol is intermittently supplemented to give an optimum concentration (about 0.01 to 5% v/v and more preferably about 0.01 to 2% v/v) which does not inhibit the growth of the strain or the production of L-threonine.

The nitrogen source (about 0.01 to 15% v/v) is chosen among ammonium sulfate, ammonium nitrate, ammonium phosphate, urea, etc. depending on the ability of the strain to utilize the nitrogen source. Further, depending on the bacteria necessary amounts (about 10% v/v or less) of organic nutrient sources such as amino acids (e.g., glutamic acid, alanine, glycine, etc.), corn steep liquor, bouillon, yeast extract, etc., inorganic salts (e.g., sulfates or hydrochlorides of Ca, Mg, Na, K, Fe, Ni and Co), vitamins (e.g., groups of Vitamin B, pantothenic acid, benzoic acid, etc.), etc. are added to prepare a culture medium.

The conditions for culturing are typically a temperature of about 20° to 40° C. and a pH of about 4 to 10 and preferably about 25° to 38° C. and a pH of about 6 to 8. The optimum conditions will depend on the particular strain used. Cultivation will generally take 2 to 7 days. The cultivation is conducted under aerobic conditions.

After cultivation, L-threonine may be recovered from the liquor by known methods such as using an ion-exchange resin, activated carbon, concentration-crystallization, etc. See, for example, *JIKKEN NOGEI KAGAKU* (*Experimental Agricultural Chemistry*), the first volume, pages 284–285, Tokyo University, Faculty of Agriculture, Department of Agricultural Chemistry, published by Asakura Shobo (1960).

The following Examples will illustrate the invention in more detail.

The quantitative assay of L-threonine was conducted by the microorganic analytical method using *Streptococcus faecalis* R ATCC 8043.

EXAMPLE 1

10 ml of a pre-culture medium containing urea 2.0 g, ammonium sulfate 7.0 g, $KH_2PO_4$ 0.5 g, $K_2HOP_4$ 0.5 g, $MgSO_4.7H_2O$ 0.5 g, $FeSO_4.7H_2O$ 2 mg, $NaCl_2$ 2 mg, $CaCl_2.2H_2O$ 2 mg, $ZnSO_4.7H_2O$ 2 mg, $MnSO_4.4-6H_2O$ 2 mg and tap water 1 liter was poured into a large test tube having an inner diameter of 24 mm, and sterilized at 120° C. for 10 minutes. 0.2 ml of ethanol was added under aseptic conditions and *Acinetobacter calcoaceticus* YK-1014 was inoculated to effect shake culture at 30° C. for 2 days. Then, 10 ml of the same culture medium as the pre-culture medium was poured into a large test tube having an inner diameter of 24 mm, sterilized at 120° C. for 10 minutes, 0.2 g of calcium carbonate which had been sterilized by dry heating was added, 0.2 ml of ethanol was added and then 0.2 ml of the pre-culture liquor was inoculated to effect shake culture at 30° C. for 4 days. Ethanol was supplemented as it was consumed. On such occasions, care was taken so that the concentration of ethanol did not exceed 3% v/v. On the 7th day after the start of cultivation, it was found that 15 mg/l of L-threonine had been accumulated. 1,000 ml of this culture liquor was centrifuged to separate the cells, the supernatant liquid was passed through a strongly acidic cation exchange resin (Diaion SK-1B, H type) to adsorb L-threonine, and 0.5 N ammonia water was passed to elute L-threonine according to a known method. The fractions containing L-threonine were concentrated, decolored using activated carbon and cold ethanol was added to obtain about 10 mg of crude crystals of L-threonine. It was confirmed by a bioassay that the crude crystals were L-threonine. The production of L-threonine was not observed with *Acinetobacter calcoaceticus* YK-1011 similarly cultured.

While the invention has been described in detail and with reference to specific embodiments thereof, it will be apparent to one skilled in the art that various changes and modifications can be made therein without departing from the spirit and scope thereof.

What is claimed is:

1. A process for producing L-threonine from a mutant bacterium which utilizes ethanol and has the ability to produce and accumulate L-threonine when culturing said bacterium, comprising aerobically culturing a mutant bacterium obtained by mutagenizing *Acenetobacter calcoaceticus* YK-1011 having FERM-P No. 5910, in a culture medium in which ethanol is the main carbon source to produce and accumulate L-threonine in a culture liquor and then recovering L-threonine.

2. The process of claim 1, wherein said mutant bacterium is *Acinetobacter calcoaceticus* YK-1014 having FERM-P No. 4818.

3. The process of claim 1, wherein said mutant bacterium is obtained by mutagenizing with N-methyl-N'-nitro-N-nitrosoguanidine.

4. The process of claim 1, wherein said mutant bacterium is cultured at a temperature of 20° to 40° C. and a pH of 4–10.

5. The process of claim 1, wherein said mutant bacterium is cultured at a temperature of 25° to 38° C. and a pH of 6–8.

6. The process of claim 1, wherein L-threonine is recovered using an ion exchange resin, activated carbon, or concentration-crystallization.

7. The process of claim 1, wherein an initial concentration of said ethanol is 1–5% volume/volume.

* * * * *